(12) United States Patent
Hou et al.

(10) Patent No.: US 10,816,531 B1
(45) Date of Patent: Oct. 27, 2020

(54) METHOD FOR CALCULATING DAILY GAS PRODUCTION RATE OF METHANE HYDRATE DEPOSIT BASED ON INFLOW PERFORMANCE RELATIONSHIP FORMULAS

(71) Applicant: China University of Petroleum (East China), Qingdao, Shandong (CN)

(72) Inventors: Jian Hou, Shandong (CN); Nu Lu, Shandong (CN); Yongge Liu, Shandong (CN); Yajie Bai, Shandong (CN); Yunkai Ji, Shandong (CN); Ermeng Zhao, Shandong (CN)

(73) Assignee: China University of Petroleum (East China) (CN)

( * ) Notice: Subject to any disclaimer, the term of this patent is extended or adjusted under 35 U.S.C. 154(b) by 0 days.

(21) Appl. No.: 16/884,263

(22) Filed: May 27, 2020

(51) Int. Cl.
| | | |
|---|---|---|
| *G01N 33/24* | (2006.01) | |
| *E21B 49/00* | (2006.01) | |
| *E21B 41/00* | (2006.01) | |
| *E21B 47/06* | (2012.01) | |
| *E21B 47/107* | (2012.01) | |
| *E21B 49/08* | (2006.01) | |

(52) U.S. Cl.
CPC ......... *G01N 33/24* (2013.01); *E21B 41/0099* (2020.05); *E21B 47/06* (2013.01); *E21B 47/107* (2020.05); *E21B 49/00* (2013.01); *E21B 49/0875* (2020.05)

(58) Field of Classification Search
CPC ....................................................... G01N 33/24
USPC ........................................................... 702/11
See application file for complete search history.

(56) References Cited

U.S. PATENT DOCUMENTS 8,775,141 B2 * 7/2014 Raphael .................. E21B 43/00
703/10
9,810,042 B1 * 11/2017 Rivas Romero ...... E21B 43/128
(Continued)

OTHER PUBLICATIONS

Nu Lu, et al., "Revised Inflow Performance Relationship for Productivity Prediction and Energy Evaluation Based on Stage Characteristics of Class III Methane Hydrate Deposits", Elsevier, dated Dec. 15, 2019, 22 pages, Science Direct, Amsterdam, NL.

*Primary Examiner* — Ricky Ngon
(74) *Attorney, Agent, or Firm* — Maine Cernota & Rardin

(57) ABSTRACT

A daily gas production rate of a methane hydrate deposit is calculated based on inflow performance relationship formulas. Step 1 determines the production stage, including the gas production rate trend of a production test and selecting an inflow performance relationship formula corresponding to the stage. Step 2 calculates basic coefficient terms related to energy conversion in the inflow performance relationship formula. Step 3 obtains other coefficient terms related to production in the inflow performance relationship formula. Step 4 predicts the gas production rate under other production pressure differences. Staged inflow performance relationship formulas characterize the complex methane hydrate deposit production performance. Gas production rate and deposit pressure under a large pressure differences are predicted through simple production tests under a small pressure difference, providing a basis for production design of the hydrate deposit and preventing accidents that may be caused by direct production under a large pressure difference.

11 Claims, 1 Drawing Sheet

(56) References Cited

U.S. PATENT DOCUMENTS

| | | | |
|---|---|---|---|
| 2014/0136112 A1* | 5/2014 | Al-Shawaf | E21B 47/00 702/6 |
| 2014/0149042 A1* | 5/2014 | Zhang | G01V 1/301 702/11 |
| 2015/0168596 A1* | 6/2015 | Khali | E21B 41/0092 702/12 |
| 2016/0312552 A1* | 10/2016 | Early | E21B 41/00 |
| 2016/0312599 A1* | 10/2016 | Adam | E21B 43/00 |
| 2016/0319655 A1* | 11/2016 | Awadh | G05B 19/402 |
| 2016/0328497 A1* | 11/2016 | Hamza | E21B 41/0035 |
| 2017/0067325 A1* | 3/2017 | Garcia Zurita | E21B 43/00 |

\* cited by examiner

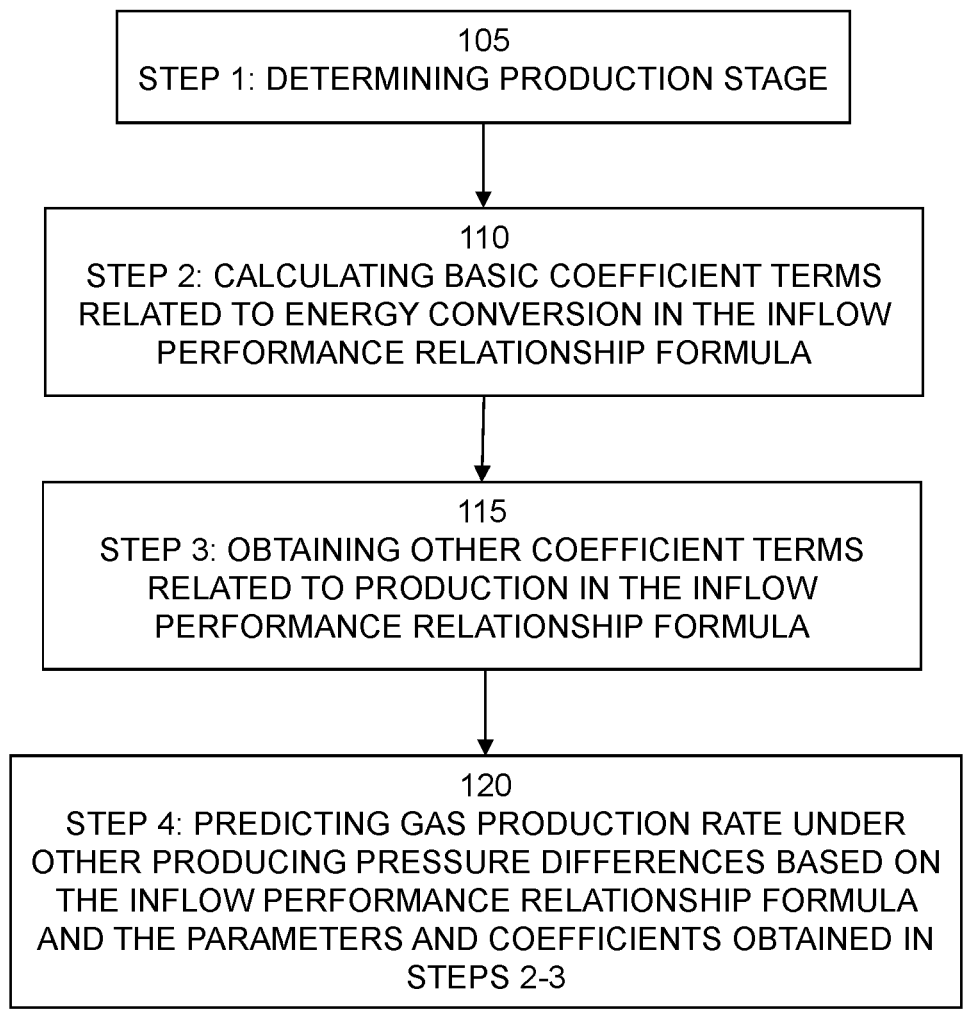
METHOD

METHOD FOR CALCULATING DAILY GAS PRODUCTION RATE OF METHANE HYDRATE DEPOSIT BASED ON INFLOW PERFORMANCE RELATIONSHIP FORMULAS

FIELD OF THE INVENTION

The present disclosure relates to a method for calculating the daily gas production rate of methane hydrate deposit based on inflow performance relationship formulas, and belongs to the technical field of petroleum development.

BACKGROUND OF THE INVENTION

Natural gas hydrate is an ice-like crystalline substance formed by natural gas and water under high pressure and low temperature conditions, which is distributed in permafrost within deep-sea sediments or land areas. It is also known as "combustible ice" because it looks like ice and can burn when exposed to fire. With a high resource density, worldwide distribution, and an extremely high resource value, the natural gas hydrate has become a long-term research hotspot in the oil and gas industry. Since the 1960s, some countries such as the United States, Japan, Germany, China, South Korea, and India have formulated natural gas hydrate exploration and development research plans. So far, more than 230 hydrate sites have been found in offshore waters and frozen soil areas, and thus a large number of natural gas hydrate hotspot research areas have emerged.

Due to the particular location and exploiting difficulty, the exploiting cost of natural gas hydrate is higher than that of conventional oil and gas reservoirs. Therefore, it is necessary to establish a methane hydrate deposit productivity prediction method. The inflow performance method is one of the methods commonly used in conventional oil and gas reservoir productivity prediction. By establishing a formula between gas production rate, bottomhole production pressure and deposit pressure, productivity under different production schemes can be quickly obtained, which is an important tool for mine production. However, the production performance of methane hydrate deposit is much more complex. Studies have shown that the gas production rate at a fixed bottomhole production pressure does not merely show a downward trend, but a two-stage condition in which it rises firstly and then falls. In addition, the production process of methane hydrate deposit also involves complex physical and chemical processes such as phase changes and changes in deposit properties. Traditional inflow performance relationship formulas and prediction methods are no longer applicable. Therefore, it is necessary to propose a new inflow performance relationship formula and a prediction method to meet the requirements of methane hydrate deposit productivity prediction and provide technical support for the study of methane hydrate deposit development.

SUMMARY OF THE INVENTION

Regarding the shortcomings of the prior art, the present disclosure provides a method for calculating the daily gas production rate of the methane hydrate deposit based on inflow performance relationship formulas, which performs a productivity prediction on the Class III methane hydrate deposit developed by depressurization based on inflow performance relationship formulas.

Embodiments include a method for calculating a daily gas production rate of a methane hydrate deposit based on inflow performance relationship formulas, including:

Step 1, determining a production stage, including determining the production stage according to the gas production rate trend of a production test of the methane hydrate deposit, and selecting an inflow performance relationship formula corresponding to the determined stage;

Step 2, calculating basic coefficient terms related to energy conversion in the inflow performance relationship formula, including obtaining initial deposit parameters and fluid parameters of the methane hydrate deposit, and substituting into related formula to calculate corresponding basic coefficient terms;

Step 3, obtaining other coefficient terms related to production in the inflow performance relationship formula, including measuring production data of a single well through one or more sets of depressurization production tests under a small production pressure difference, and substituting these production data into the selected inflow performance relationship formula to obtain other pending coefficient terms under the same deposit condition and the same recovery percent; and Step 4, predicting a gas production rate under other production pressures, including calculating production rates under other bottomhole production pressures based on the inflow performance relationship formula and the parameters and coefficients obtained in Steps 2-3.

Wherein the methane hydrate deposit in Step 1 refers to the Class III natural gas methane hydrate deposit according to its geological type, which only consists of a single hydrate layer, and is surrounded by impermeable mudstones at its top and bottom.

Wherein, in Step 1, the hydrate depressurization recovery process is divided into two stages: the gas production rate ascent stage, and the gas production rate decline stage. When the gas production rate under the same production pressure continues to rise within a short production time, the hydrate depressurization process is in the ascent stage; otherwise, the hydrate depressurization process is in the decline stage.

Wherein the inflow performance relationship formula of the ascent stage in Step 1 is:

$$\text{Ln}(q_g) = A_1 \cdot \text{Ln}\left[\left(B \cdot \left(1 - \frac{N_p}{N}\right)^{\frac{\Delta P_{max,T=0}}{\Delta P_{max}}} \cdot (P_i - P_r) + P_r\right)^2 - P_{wf}^2\right] + A_2,$$

wherein $q_g$ is the gas production rate (m³/day), $A_1$, $A_2$, and B are coefficients, $N_p/N$ is the gas recovery percent, $P_i$ is the initial average pressure (MPa) of the methane hydrate deposit, $P_r$ is the average pressure (MPa) of the methane hydrate deposit, $P_{wf}$ is the bottomhole production pressure (MPa), and $$\frac{\Delta P_{max,T=0}}{\Delta P_{max}}$$

is a ratio of the maximum production pressure difference under an initial deposit condition to the maximum production pressure difference during the production.

Wherein the inflow performance relationship formula of the decline stage in Step 1 is:

$$\frac{q_g}{q_{gmax}} = 1 - C\left(\frac{P_{wf} - P_{ice}}{P_r - P_{ice}}\right) - (1-C)\left(\frac{P_{wf} - P_{ice}}{P_r - P_{ice}}\right)^2,$$

wherein $q_{gmax}$ is a gas production rate (m³/day) corresponding to the minimum bottomhole production pressure, C is a coefficient, and $P_{ice}$ is a pressure (MPa) corresponding to the quadruple point of the hydrate. Wherein the minimum bottomhole production pressure is set to the methane hydrate quadruple point pressure. Wherein the parameters obtained through methods such as well logging, production test, and the like in Step 2 include initial deposit pressure, initial deposit temperature, initial average hydrate saturation, fluid salinity, and thickness of the methane hydrate layer. Wherein the related formula for calculating the basic coefficient terms related to energy conversion in inflow performance relationship formula coefficients of the ascent stage in Step 2 is:

$$B = \left(2.056 - 0.254 \cdot \frac{(0.0548 + 7.154 \cdot S_{irG})^{3.97 - 0.795 \cdot N_g}}{H^{-0.0847} - 0.846}\right),$$

wherein $S_{irG}$ is the irreducible gas saturation of the deposit fluid, $N_g$ is the gas index in the calculation of gas relative permeability (Stone modified model), and H is the thickness (m) of the hydrate layer. Wherein the related formula for calculating the basic coefficient terms related to energy conversion in inflow performance relationship formula coefficients of the decline stage in Step 2 is:

$$C = 0.88 - 0.062 \cdot \frac{S_H^{0.38} \cdot (S + 77.2)}{H^{1.27}} - 0.012 \cdot \text{Ln}(S_H^{-0.65} - 1.3) \cdot (S - 4.61),$$

wherein $S_H$ is the hydrate saturation of the hydrate layer of the methane hydrate deposit, and S is the salinity (%) of the methane hydrate deposit. Wherein the production test of the single well in Step 3 is carried out by depressurization at a fixed bottomhole production pressure, and the difference between the bottomhole production pressure applied in the test and the deposit pressure should not exceed half of the initial average deposit pressure.

Wherein the parameters obtained in the ascent stage in Step 3 are pending coefficients $A_1$ and $A_2$, which need to be calculated by substituting the gas production rate and deposit pressure data of no less than two sets of production tests into the corresponding inflow performance relationship formula. The specific calculation adopts the regression method, and a non-linear regression model is established according to the inflow performance relationship formula, with the gas production rate as a dependent variable and the deposit pressure as an independent variable, and the most appropriate pending coefficient is then determined by the least-square method.

Wherein the parameter obtained in the decline stage in Step 3 is the maximum gas production rate, which needs to be calculated by substituting the gas production rate and deposit pressure data of no less than one set of production test data into the corresponding inflow performance relationship formula. The specific calculation may directly adopt the substitution formula or the regression method. A non-linear regression model is established according to the inflow performance relationship formula, with the gas production rate as a dependent variable and the deposit pressure as an independent variable, and the most appropriate pending coefficient is then determined by the least-square method.

The present disclosure solves the problem that the methane hydrate deposit production performance is complex in change and difficult to characterize through a staged inflow performance relationship formula. The method adopts staged inflow performance relationship formulas to characterize the complex methane hydrate deposit production performance. Also, the gas production rate and deposit pressure under a large pressure difference can be predicted through one or more sets of simple production tests under a small pressure difference, so as to provide a theoretical basis for the production design of the hydrate deposit and to prevent production accidents that may be caused by direct production under a large production pressure difference, which provides guarantee for efficient and stable production of the methane hydrate deposit.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 1 is a flow diagram of calculating a daily gas production rate of a methane hydrate deposit based on inflow performance relationship formulas according to an embodiment of the present disclosure.

DETAILED DESCRIPTION

A detailed description of illustrative embodiments will now be described with reference to the various FIGURES. Although this description provides a detailed example of possible implementations, it should be noted that the details are intended to be exemplary and in no way limit the scope of the application. It should be noted that in this text, the terms "methane hydrate deposit" and "deposit" and can be used interchangeably.

FIG. 1 depicts a method 100 for calculating the daily gas production rate of a methane hydrate deposit based on inflow performance relationship formulas is provided. FIG. 1 is a flow diagram of calculating a daily gas production rate of a methane hydrate deposit based on inflow performance relationship formulas according to an embodiment of the present disclosure. As shown in FIG. 1, the method includes:

Step 1 105, determining production stage, including determining the production stage according to the gas production rate trend of a production test of the methane hydrate deposit, and selecting an inflow performance relationship formula corresponding to the determined stage;

Step 2 110, calculating basic coefficient terms related to energy conversion in the inflow performance relationship formula, including obtaining initial deposit parameters and fluid parameters of the methane hydrate deposit and substituting into related formula to calculate corresponding basic coefficient terms;

Step 3 115, obtaining other coefficient terms related to production in the inflow performance relationship formula, including measuring production data of a single well through one or more sets of depressurization production tests under a small production pressure difference, and substituting these production data into the selected inflow performance relationship formula to obtain other pending coefficient terms under the same deposit condition and the same recovery percent; and Step 4 120, predicting the gas production rate under other production pressure differences, including calculating production rates under other bottomhole production pressures based on the inflow performance relationship formulas and the parameters and coefficients obtained in Steps 2-3.

The inventive concept will now be described with reference to the following two examples.

Example I

There is a Class III methane hydrate deposit with an initial deposit pressure of 11.32 MPa, a hydrate saturation of 0.6, salinity of 0, a hydrate layer thickness of 20 m, an irreducible gas saturation of 0.05, and a gas index of 3. There is a production well in the center of the deposit. During the production test, the production pressure is 6 MPa, and the measured gas production rate is $2.012 \times 10^4$ m³/day. It is found that the gas production rate shows a downward trend. The corresponding deposit pressure during production is 6.429 MPa. Assuming the deposit pressure is constant, find out the corresponding gas production rate when the production pressure drops to 4 MPa under the same deposit condition. Specific solution steps are as follows:

Step 1, since the gas production rate at the testing point shows a downward trend, the production is in a decline stage, the inflow performance relationship formula in the decline stage:

$$\frac{q_g}{q_{gmax}} = 1 - C\left(\frac{P_{wf} - P_{ice}}{P_r - P_{ice}}\right) - (1 - C)\left(\frac{P_{wf} - P_{ice}}{P_r - P_{ice}}\right)^2 \text{ is adopted;}$$

Step 2, coefficient C is calculated, and $S_H$=0.6, H=20 m and Xs=0 ($P_{ice}$=2.63 MPa) are substituted into formula:

$$C = 0.88 - 0.062 \cdot \frac{S_H^{0.38} \cdot (S + 77.2)}{H^{1.27}} - 0.012 \cdot \text{Ln}(S_H^{-0.65} - 1.3) \cdot (S - 4.61)$$

thereby, after calculation, C=0.643;

Step 3, the maximum gas production rate is obtained, when $P_r$=6.429 MPa, $P_{wf}$=6 MPa, according to the inflow performance relationship formula, $q_{gmax}$=13.595×10⁴ m³/day, at this time the inflow performance relationship formula is:

$$\frac{q_g}{q_{gmax}} = 1 - 0.648\left(\frac{P_{wf} - 2.63}{P_r - 2.63}\right) - 0.352\left(\frac{P_{wf} - 2.63}{P_r - 2.63}\right)^2;$$

and

Step 4, $P_{wf}$=4 MPa is substituted into the above formula to obtain that $q_g$=9.788×10⁴ m³/day.

Example II

If the production pressure during the production test is 6 MPa, the gas production rate is $1.492 \times 10^4$ m³/day when recovery efficiency is 2.5%, and, after maintaining the production pressure for a period of time, the gas production rate tested again is $2.854 \times 10^4$ m³/day when recovery efficiency is 5%. It was found that the gas production rates show an upward trend during the two tests. The corresponding deposit pressures during production are 8.751 MPa and 7.995 MPa, respectively. Assuming the deposit conditions are the same, when the deposit pressure is 7.995 MPa and the recovery efficiency is 5%, find out the corresponding gas production rate when the production pressure drops to 4 MPa under the same deposit condition.

Specific solution steps are as follows:

Step 1, since the gas production rate at the testing point shows an upward trend, the production is in an ascent stage, the inflow performance relationship formula in the ascent stage:

$$\text{Ln}(q_g) = A_1 \cdot \text{Ln}\left[\left(B \cdot \left(1 - \frac{N_p}{N}\right)^{\frac{\Delta P_{max,T=0}}{\Delta P_{max}}} \cdot (P_i - P_r) + P_r\right)^2 - P_{wf}^2\right] + A_2$$

is adopted;

Step 2, coefficient B is calculated, and $S_{irG}$=0.05, Ng=3.0 and H=20 m are substituted into formula:

$$B = \left(2.056 - 0.254 \cdot \frac{(0.0548 + 7.154 \cdot S_{irG})^{3.97 - 0.795 \cdot N_g}}{H^{-0.0847} - 0.846}\right)$$

thereby, after calculation, B=2.946;

$$P_r = 8.751 \text{ MPa}, P_{wf} = 6 \text{ MPa}, \frac{N_p}{N} = 0.025, q_g = 2.012 \times 10^4$$

Step 3, coefficients $A_1$ and $A_2$ are calculated, and $P_i$=11.32 MPa, m³/day are substituted into the formula to obtain that $$9.610 = 5.395 A_1 + A_2; P_i = 11.32 \text{ MPa}, P_r = 7.995 \text{ MPa},$$

$$P_{wf} = 6 \text{ MPa}, \frac{N_p}{N} = 0.05, q_g = 2.854 \times 10^4$$

m³/day are substituted into the formula to obtain that $10259=5.5338A_1+A_2$; the two formulas adopt a simultaneous solution to obtain that $A_1$=4.8505, $A_2$=−16.5827 by a regression method, at this time the inflow performance relationship formula is:

$$\text{Ln}(q_g) = 4.8505 \cdot$$

$$\text{Ln}\left[\left(2.946 \cdot \left(1 - \frac{N_p}{N}\right)^{\frac{\Delta P_{max,T=0}}{\Delta P_{max}}} \cdot (P_i - P_r) + P_r\right)^2 - P_{wf}^2\right] - 16.5827;$$

and

Step 4, $$P_i = 11.32 \text{ MPa}, P_{wf} = 4 \text{ MPa}, P_r = 7.995 \text{ MPa}, \frac{N_p}{N} = 0.05$$

are substituted into the above formula to obtain that $q_g$=4.640×10⁴ m³/day.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for calculating the daily gas production rate of a methane hydrate deposit based on inflow performance relationship formulas, comprising:
    in a Step 1, determining a production stage, including determining the production stage according to a gas production rate trend of a production test of the methane hydrate deposit, and selecting an inflow performance relationship formula corresponding to the determined stage, wherein the production stage in Step 1 comprises a gas production rate ascent stage and a gas production rate decline stage; and when a gas production rate under a same production pressure continues to rise within a short production time, the production stage is in the ascent stage; otherwise the production stage is in the decline stage;
    in a Step 2, calculating basic coefficient terms related to energy conversion in the inflow performance relationship formula, including obtaining initial deposit parameters and fluid parameters of the methane hydrate deposit and substituting into related formula to calculate corresponding basic coefficient terms;
    in a Step 3, obtaining other coefficient terms related to production in the inflow performance relationship formula, including measuring production data of a single well through one or more sets of depressurization production tests under a small production pressure difference, and substituting these production data into the selected inflow performance relationship formula to obtain other pending coefficient terms under a same deposit condition and a same recovery percent;
    in a Step 4, predicting a gas production rate under other production pressure differences, comprising calculating production rates at other bottomhole production pressures based on the inflow performance relationship formula and parameters and the coefficients obtained in Steps 2-3; and
    thereby predicting the gas production rate of the methane hydrate deposit.

2. The method according to claim 1, wherein the methane hydrate deposit in Step 1 refers to a Class III natural gas methane hydrate deposit according to a geological type, only consists of a single hydrate layer, and is surrounded by impermeable mudstones at a top and bottom.

3. The method according to claim 1, wherein the inflow performance relationship formula of an ascent stage in Step 1 is:

$$\operatorname{Ln}(q_g) = A_1 \cdot \operatorname{Ln}\left[\left[B \cdot \left(1 - \frac{N_p}{N}\right)^{\frac{\Delta P_{max,T=0}}{\Delta P_{max}}} \cdot (P_i - P_r) + P_r\right]^2 - P_{wf}^2\right] + A_2$$

wherein $q_g$ is a gas production rate (m$^3$/day), $A_1$, $A_2$, and B are coefficients, $N_p/N$ is a gas recovery percent, $P_i$ is an initial pressure (MPa) of the methane hydrate deposit, $P_r$ is an average deposit pressure (MPa) of the methane hydrate deposit, $P_{wf}$ is a bottomhole production pressure (MPa), and $$\frac{\Delta P_{max,T=0}}{\Delta P_{max}}$$

is a ratio of a maximum production pressure difference under an initial deposit condition to a maximum production pressure difference during production.

4. The method according to claim 1, wherein the inflow performance relationship formula of a decline stage in Step 1 is:

$$\frac{q_g}{q_{gmax}} = 1 - C\left(\frac{P_{wf} - P_{ice}}{P_r - P_{ice}}\right) - (1 - C)\left(\frac{P_{wf} - P_{ice}}{P_r - P_{ice}}\right)^2,$$

wherein $q_{gmax}$ is a gas production rate (m$^3$/day) corresponding to a minimum bottomhole production pressure, C is a coefficient, and $P_{ice}$ is a pressure (MPa) corresponding to a quadruple point of a hydrate.

5. The method according to claim 4, wherein the minimum bottomhole production pressure is set to the methane hydrate quadruple point pressure.

6. The method according to claim 1, wherein the parameters obtained through methods including well logging and production test in Step 2 comprise initial deposit pressure, initial deposit temperature, initial average hydrate saturation, fluid salinity, and thickness of the methane hydrate layer.

7. The method according to claim 1, wherein a related formula for calculating the basic coefficient terms related to energy conversion of an ascent stage in Step 2 is:

$$B = \left(2.056 - 0.254 \cdot \frac{(0.0548 + 7.154 \cdot S_{irG})^{3.97 - 0.795 \cdot N_g}}{H^{-0.0847} - 0.846}\right),$$

wherein $S_{irG}$ is an irreducible gas saturation of a deposit fluid, $N_g$ is a gas index in calculation of gas relative permeability, and H is a thickness of a hydrate layer of the methane hydrate deposit.

8. The method according to claim 1, wherein a related formula for calculating the basic coefficient terms related to energy conversion of a decline stage in Step 2 is:

$$C = 0.88 - 0.062 \cdot \frac{S_H^{0.38} \cdot (S + 77.2)}{H^{1.27}} - 0.012 \cdot \text{Ln}(S_H^{-0.65} - 1.3) \cdot (S - 4.61),$$

wherein $S_H$ is a hydrate saturation of a hydrate layer of the methane hydrate deposit, and S is a salinity (%) of the methane hydrate deposit.

9. The method according to claim 1, wherein a production test of the single well in Step 3 is carried out by depressurization at a fixed bottomhole production pressure, and a difference between a bottomhole production pressure applied in the production test and a deposit pressure should not exceed half of an initial average deposit pressure.

10. The method according to claim 1, wherein parameters obtained in an ascent stage in Step 3 are pending coefficients $A_1$ and $A_2$, and is calculated by substituting gas production rate and deposit pressure data of no less than two sets of production tests into a corresponding inflow performance relationship formula.

11. The method according to claim 1, wherein a parameter obtained in a decline stage in Step 3 is a maximum gas production rate, and is calculated by substituting gas production rate and deposit pressure data of no less than one set of production tests into a corresponding inflow performance relationship formula.

* * * * *